United States Patent
Nussinovitch et al.

[11] Patent Number: 5,827,974
[45] Date of Patent: Oct. 27, 1998

[54] SYSTEM FOR MEASURING THE CRISPINESS OF MATERIALS

[76] Inventors: Amos Nussinovitch, 48 Fin Ganim Street, Petah-Tiqua, Israel; Eyal Mey-Tal, 15 Chashmonaim Street, Rehovot, Israel

[21] Appl. No.: 734,960

[22] Filed: Oct. 22, 1996

Related U.S. Application Data

[63] Continuation-in-part of Ser. No. 383,126, Feb. 3, 1996, abandoned.

[51] Int. Cl.[6] .................................................. G01N 3/08
[52] U.S. Cl. ................................................ 73/821; 73/866
[58] Field of Search ........................... 73/821, 834, 866, 73/851, 573

[56] References Cited

U.S. PATENT DOCUMENTS

| | | | |
|---|---|---|---|
| 5,005,415 | 4/1991 | Holroyd | 73/801 |
| 5,289,387 | 2/1994 | Higo et al. | 73/801 |

FOREIGN PATENT DOCUMENTS

| | | | |
|---|---|---|---|
| 1647356 | 5/1991 | U.S.S.R. | 73/801 |

OTHER PUBLICATIONS

Lord et al. "Acoustic Emission Behavior of Sand . . . ", Material Eval; May 1976 pp. 103–108.

James et al. "Acoustic Emmission Test Facility", The Review of Scientif Inst. vol. 42, No. 8 Aug. 1971, pp. 1131–1136.

*Primary Examiner*—Richard Chilcot
*Assistant Examiner*—Max H. Noori
*Attorney, Agent, or Firm*—Evenson, McKeown, Edwards & Lenahan, PLLC

[57] ABSTRACT

A device and a method for the determination of a Fractal number representative of the crispiness and crunchiness of various materials, especially edible materials. The material to be tested is crushed by the application of a given force by a piston moving in a cylinder, which crushes such substance, whereby noise is created, recorded and subsequently evaluated. A preferred device comprises a microphone positioned beneath a baseplate in the cylinder of the device, on which plate the sample is positioned, which microphone picks up the noise which is subsequently evaluated. According to a preferred embodiment an opening is provided in the cylinder for inserting and removing the sample to be tested.

6 Claims, 2 Drawing Sheets

SYSTEM FOR MEASURING THE CRISPINESS OF MATERIALS

This is a continuation-in-part application of Ser. No. 08/383,126, filed on Feb. 3, 1996 now abandoned.

FIELD OF INVENTION

The invention relates to a device and to a method for the determination of the crunchy properties of various substances, and especially of edibles.

The device and the method are based on the gradual crushing of the tested substance, while the noise created thereby is sensed by voice sensor such as a microphone and evaluated.

The device of the invention can be attached as attachment to conventional machines, which are on the market, such as Instron, JJ, Lloyd, etc., which are used to determine mechanical properties of solid foodstuffs and other materials.

Amongst others there can be evaluated the freshness of products like cereals, waffles, snacks, noodles and similar products, sugar cubes, etc.

The device comprises a generally cylindrical body in which there is located a base plate on which the material to be tested is supported, and adjacent or below which there is positioned a microphone, which is protected by said base plate. There is provided a piston which moves inside said cylindrical member, and which is moved downwards at a predetermined velocity and deformation rate. The piston exerts a certain pressure on the tested substance and while this is disintegrated, the noise created is picked up by the microphone. A voice card inserted into a computer serves to pick up the noise thus created and this is evaluated by means of a certain algorithm which generally provides a numerical result which is indicative of the crunchiness of the substance. This number is indicative of the "roughness" of the produce test. The measurement gives also an indication of the humidity of certain substances, and the higher such humidity, the greater the change in the noises picked up by the microphone. It is generally possible to obtain a linear curve between the degree of roughness and crispiness and the percentage of water content of the product.

The device is illustrated with reference to the enclosed schematical Figure, which is not according to scale and in which 11 is a cylinder, in which piston 12 can move up and down, pressure being exerted on it by drive 13. There is provided at the bottom of the cylinder 11, a protective plate 14, on which the substance to be tested is placed. This plate protects microphone 15 which is suitably connected by wire 18 to convey noises originating from the crushing of the product being tested as it is disintegrated by such pressure, and evaluation is being done by computer means provided with a voice card.

There is provided a base 16 which also serves as sound isolator and the cylinder 11 is surrounded by isolating sleeve 17. There is provided an opening in the cylinder 11 and isolating sleeve 17, which is closed by member 19 and 19' equipped with handle 20 for inserting and removing a sample which is placed on support plate 14.

Figure 1:
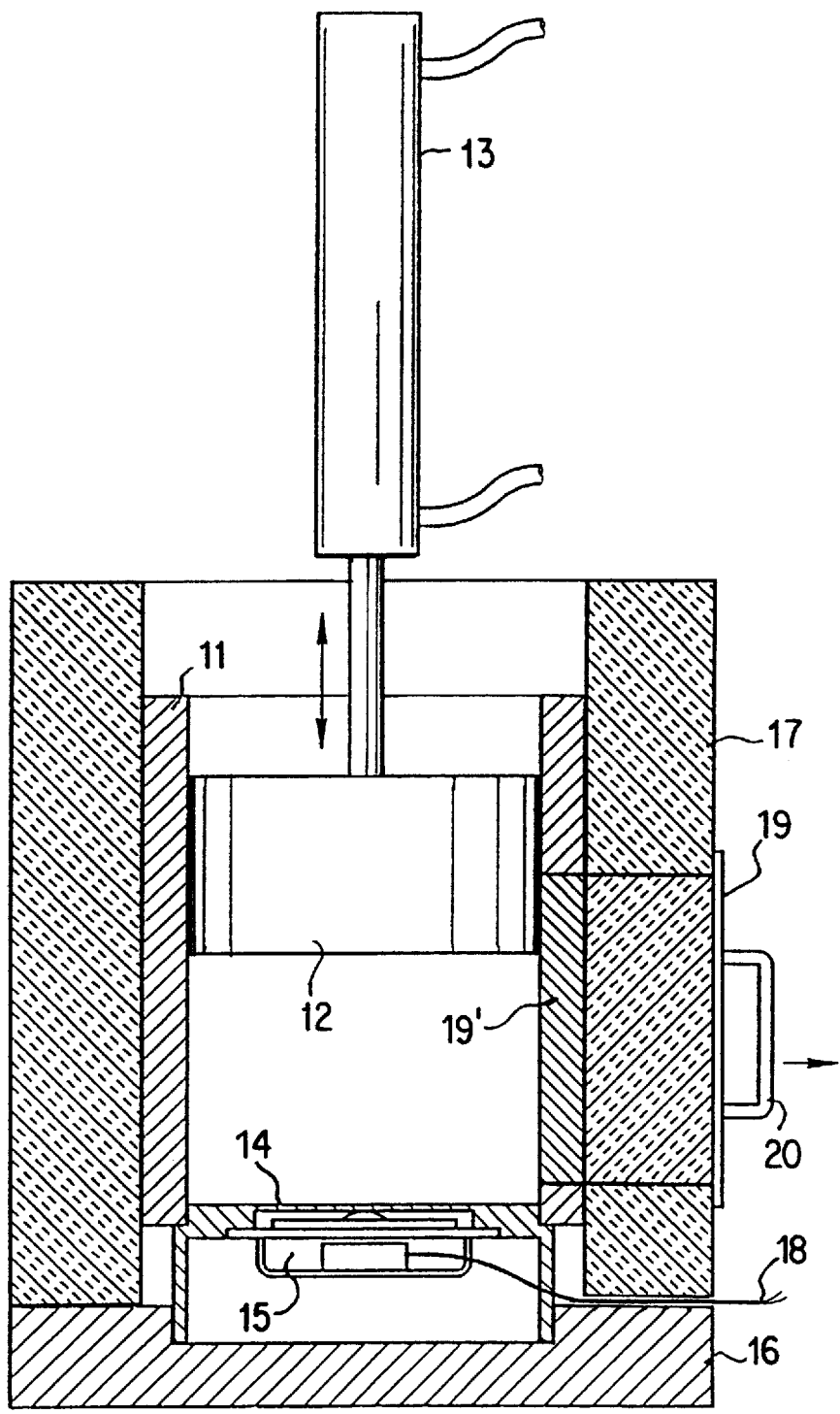
FIG. 1 is a schematic of the test apparatus.
Figure 2:
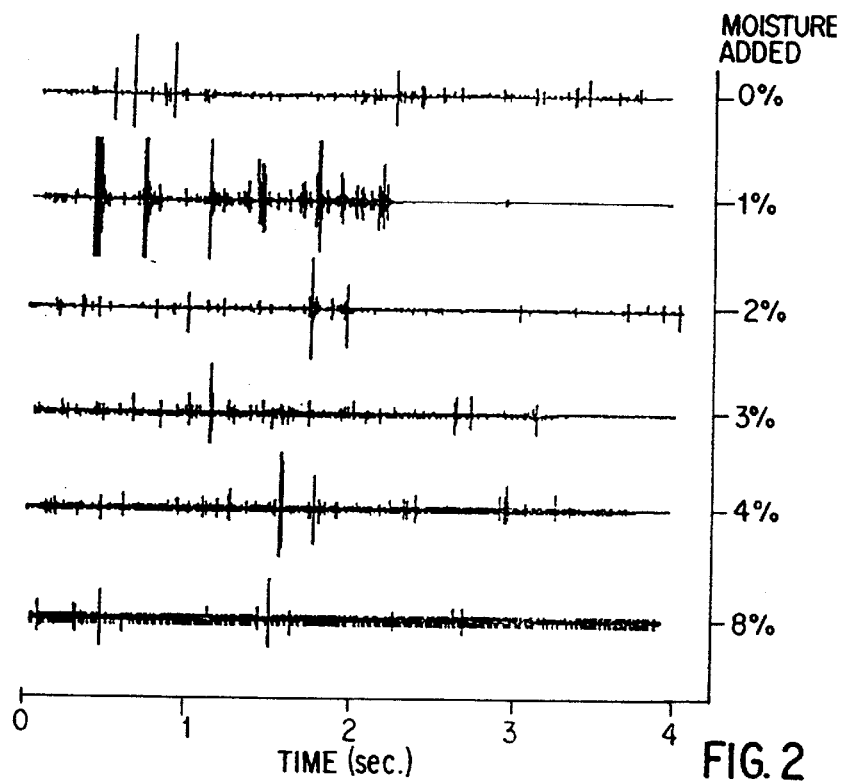
FIG. 2 is a graph illustrating noise records obtained by the crushing of sugar cubes at various degrees of humidity (Example 1) and FIG. 3 is a noise record of gradual crushing of croutons at varying percentages of moisture added to the tested product (Example 2).
Figure 3:
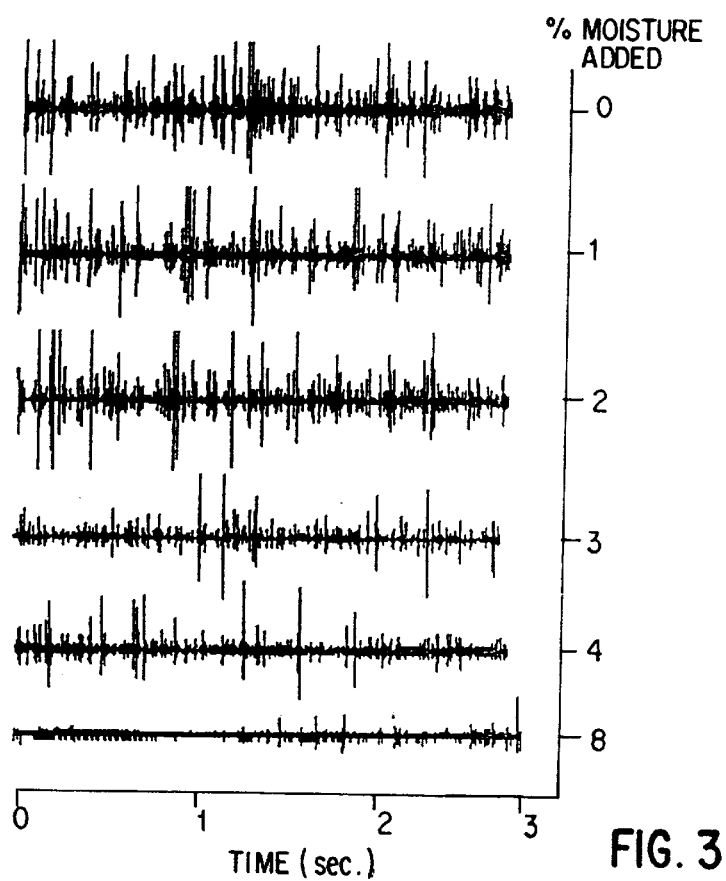

The simple device has a wide application for many products and the above are but a few samples of these.

The procedure we followed to derive the fractal dimension (fractal number) of the acoustical graphs is as follows. The experimental curve Y(x), where Y is the noise amplitude and x is the time is fitted ("smoothed") by, for example a polynomial model and then transformed into a normalized relationship R(x) where the dimensionless parameter R(x) has been defined by A. M. Barrett et al, 1992.

$$R(x)=[Y(x)-Y^*(x)]/Y^*(x)$$

$Y^*(x)$ being the corresponding fitted value at x.

The apparent fractal dimension of the rugged line R(x) can then be determined using the "Blanket alogarithm", which has also been used in the characterization of rugged surface textures. The creation of successive layers of the "blanket" filling the "valleys" at each iteration is achieved using the equation:

$$B_{n+1}(l)=\max \{B_n(i)+1, \max [B_n(i-1), B_n(i+1)]\}$$

where B (i) is the blanket's half thickness at location x=i and n the iteration number, i.e. n=1, 2, 3. . .

This equation is based on S. Peleg et al., 1984.

A corresponding Richardsom plot can be produced by calculating the line's length at each iteration from the cumulative "blanket area", A(n), divided by its corresponding thickness. The line's length at each iteration is therefore defined as:

$$L(n)=A(n)/2n$$

The fractal dimension D of R(x) is calculated by $$D=1+|\text{tag } \delta|$$

where tag δ is the slope of the linear portion of the log-log plot of the line's length [L(n(] vs the blankets half thickness (n).

REFERENCES

A. M. Barrett, M. D. Normand, M. Peleg, E. J. Ross: Characterization of the jagged stress-strain relationships of puffed extrudates using the fast Fourier transform and fractal analysis. Food Sci. 53, 227–232, 235 (1992).

S. Peleg, J. Naor, R. Hartley, D. Avnir: Multiple resolution texture analysis and classification. IEEE. Trans Pattern Anal. Mach. Intlligence. 6, 518–523 (1984).

The invention is illustrated by way of example with reference to the following Examples:

EXAMPLE 1

Dry sugar cubes were crushed, which had a solid content of about 97.95% on the average. Humidity of 1%, 2%, 3%, 4% and 8% was added. The cubes were crushed in an Instron tester to which there was attached a device according to the invention. Acoustic recordings were obtained and registered, which are attached herewith. The "roughness" of the records was evaluated and it was found to decrease with an increase of humidity. The results are:

| Per Cent Humidity | Fractal Number | Maximum Force for Crushing kg/cm$^2$ |
|---|---|---|
| 0 | 1.32 | 25.7 |
| 1 | 1.23 | 13.0 |
| 2 | 1.19 | 7.5 |
| 3 | 1.16 | 7.5 |
| 4 | 1.13 | 7.4 |
| 8 | 1.10 | 1.2 |

EXAMPLE 2

A similar measurement was made with croutons, having a starting water content of about 0.25%. To this there were added varying percentages of water, and the results were:

| Added Humidity % | Fractal Number |
|---|---|
| 0 | 1.62 |
| 1 | 1.39 |
| 2 | 1.37 |
| 3 | 1.33 |
| 4 | 1.30 |
| 8 | 1.18 |

The "roughness" of the recording decreases with an increase of humidity. As stated above, the novel device can be used for similar determinations with a very wide spectrum of products.

There is advantageously provided an opening, at the lower part of the cylinder, with closure means, for the rapid introduction and removal of samples.

We claim:

1. A device for determining the crispiness and behavior of a material during crushing of the material by measuring the Fractal number which comprises a piston, a support located at the bottom of a cylinder to support the material during crushing, and a microphone protected by said support and located beneath or adjacent to said support, said microphone being connected to a means for picking up noise created during crushing of the material and evaluating the noise to obtain a Fractal number, and said piston being provided with means for gradually lowering the piston inside the cylinder and for exerting a predetermined pressure on the material.

2. A device according to claim 1, where the output of the microphone is connected to a computer provided with a voice card and with algorithm means for evaluating the noise created during the crushing process.

3. A method for evaluating the crispiness of a material, and its moisture content, which comprises crushing the material in a cylindrical setup by means of a piston which is lowered so as to crush the tested material being located on a base plate, and recording by means of a microphone or other noise transducer the noise created during the crushing and evaluating the noise to obtain a Fractal number.

4. A method as claimed in claim 3, where the tested material is selected from cereals, waffles, snacks, noodles and sugar cubes.

5. A method according to claim 3, where the degree of humidity of said material is determined by evaluating the noise created during the crushing, the evaluation being effected by comparison with stored data or by comparison with curves obtained with standard samples.

6. A device as claimed in claim 1, further comprises an opening located at a lower part of the cylinder, for inserting and removing a sample.

* * * * *